(12) United States Patent
Balding

(10) Patent No.: US 6,447,474 B1
(45) Date of Patent: Sep. 10, 2002

(54) AUTOMATIC FEVER ABATEMENT SYSTEM

(75) Inventor: David P. Balding, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/396,200

(22) Filed: Sep. 15, 1999

(51) Int. Cl.$^7$ .......................... A61M 31/00; A61F 7/12
(52) U.S. Cl. ........................ 604/66; 604/503; 604/113
(58) Field of Search ............................. 604/65–67, 503, 604/506, 890.1, 891.1, 31

(56) References Cited

U.S. PATENT DOCUMENTS

| | | | |
|---|---|---|---|
| 2,058,780 A | 10/1936 | Elliott ........................... 128/401 |
| 2,077,453 A | 4/1937 | Albright ...................... 128/254 |
| 2,308,484 A | 1/1943 | Auzin et al. ...................... 18/58 |
| 3,125,096 A | 3/1964 | Antiles et al. ............... 128/401 |
| 3,142,158 A | 7/1964 | Podolsky ........................... 62/3 |
| 3,238,944 A | 3/1966 | Hirschhorn ................. 128/400 |
| 3,282,267 A | 11/1966 | Eidus ........................... 128/399 |
| 3,327,713 A | 6/1967 | Eidus ........................... 128/399 |
| 3,425,419 A | 2/1969 | Dato ........................... 128/400 |
| 3,504,674 A | 4/1970 | Swenson et al. .......... 128/303.1 |
| 3,738,372 A | 6/1973 | Shioshvili ................... 128/400 |
| 3,776,241 A | 12/1973 | Magilton et al. ............ 128/400 |
| 3,897,790 A | 8/1975 | Magilton et al. ............ 128/400 |
| 3,913,581 A | 10/1975 | Ritson et al. ............. 128/303.1 |
| 4,010,795 A | 3/1977 | Stenberg ....................... 165/46 |
| 4,111,209 A | 9/1978 | Wolvek et al. ............... 128/400 |
| 4,154,245 A | 5/1979 | Daily ........................... 128/400 |
| 4,249,923 A | 2/1981 | Walda .......................... 62/394 |
| 4,298,006 A | 11/1981 | Parks ........................... 128/399 |
| 4,416,280 A | 11/1983 | Carpenter et al. .......... 128/399 |
| 4,416,281 A | 11/1983 | Cooper et al. ............... 128/400 |
| 4,583,969 A | 4/1986 | Mortensen .................... 604/49 |
| 4,672,962 A | 6/1987 | Hershenson ............. 128/303.1 |
| 4,745,922 A | 5/1988 | Taylor ......................... 128/380 |
| 4,748,979 A | 6/1988 | Hershenson ............. 128/303.1 |
| 4,750,493 A | 6/1988 | Brader ......................... 128/380 |
| 4,754,752 A | 7/1988 | Ginsberg et al. ........ 128/303.12 |
| 4,759,349 A | 7/1988 | Betz et al. ...................... 128/6 |
| 4,791,930 A | 12/1988 | Suzuki et al. ............... 128/399 |
| 4,813,210 A | 3/1989 | Masuda et al. ............... 53/425 |
| 4,823,076 A | 4/1989 | Haines et al. ........... 324/121 R |
| RE32,983 E | 7/1989 | Levy ....................... 428/36.92 |
| 4,844,074 A | 7/1989 | Kurucz ........................ 128/401 |
| 4,850,958 A | 7/1989 | Berry et al. .................. 604/26 |
| 4,860,744 A | 8/1989 | Johnson et al. .......... 128/303.1 |
| 4,883,455 A | 11/1989 | Leonard ......................... 604/4 |
| 4,899,741 A | 2/1990 | Bentley et al. ............... 606/27 |

(List continued on next page.)

FOREIGN PATENT DOCUMENTS

| WO | WO 98/26831 | 6/1998 | .......... A61M/25/00 |
|---|---|---|---|
| WO | WO 98/31312 | 7/1998 | ............. A61F/7/12 |

*Primary Examiner*—Michael J. Hayes
(74) *Attorney, Agent, or Firm*—Arlyn Alonzo; John Rogitz; Lyon & Lyon

(57) ABSTRACT

A machine-driven automatic fever abatement system treats or prevents fever in hospital patients by administering medication, coolant, or other antipyretic means. The system includes a path, a flow device, a source of treatment substance, fever-characteristic sensors, and a controller. The path may be an open-ended structure, such as a tube, or a closed-ended structure such as a catheter with a sealed, internal path. The path is coupled to one or more bodily sites of the patient. The path is coupled to the flow device, which is itself attached to the source. The source contains a treatment substance such as medication (in the case of an open-ended path) or a coolant (in the case of a closed-ended path). One or more fever characteristic sensors are attached to various sites on the patient, for sensing temperature, metabolic rate, and/or other fever-affected physiological properties.

7 Claims, 4 Drawing Sheets

U.S. PATENT DOCUMENTS

| | | | | |
|---|---|---|---|---|
| 4,920,963 A | | 5/1990 | Brader | 128/402 |
| 4,941,475 A | | 7/1990 | Williams et al. | 128/692 |
| 4,987,896 A | | 1/1991 | Nakamatsu | 128/399 |
| RE33,561 E | | 3/1991 | Levy | 428/36.92 |
| 5,019,075 A | | 5/1991 | Spears et al. | 606/7 |
| 5,021,045 A | | 6/1991 | Buckberg et al. | 604/53 |
| 5,036,462 A | * | 7/1991 | Kaufman et al. | 128/668 |
| 5,041,089 A | | 8/1991 | Mueller et al. | 604/96 |
| 5,066,578 A | | 11/1991 | Wikman-Coffelt | 435/1 |
| 5,078,713 A | | 1/1992 | Varney | 606/23 |
| 5,092,841 A | | 3/1992 | Spears | 604/96 |
| 5,098,376 A | | 3/1992 | Berry et al. | 604/26 |
| 5,106,360 A | | 4/1992 | Ishiwara et al. | 600/2 |
| 5,139,496 A | | 8/1992 | Hed | 606/23 |
| 5,147,355 A | | 9/1992 | Friedman et al. | 606/23 |
| 5,147,385 A | | 9/1992 | Beck et al. | 623/1 |
| 5,151,100 A | | 9/1992 | Abele et al. | 606/28 |
| 5,158,534 A | | 10/1992 | Berry et al. | 604/4 |
| 5,174,285 A | | 12/1992 | Fontenot | 128/400 |
| 5,182,317 A | | 1/1993 | Winters et al. | 523/112 |
| 5,191,883 A | | 3/1993 | Lennox et al. | 128/401 |
| 5,196,024 A | | 3/1993 | Barath | 606/159 |
| 5,211,631 A | | 5/1993 | Sheaff | 604/113 |
| 5,230,862 A | | 7/1993 | Berry et al. | 422/48 |
| 5,248,312 A | | 9/1993 | Langberg | 606/28 |
| 5,250,070 A | | 10/1993 | Parodi | 606/194 |
| 5,257,977 A | | 11/1993 | Eshel | 604/113 |
| 5,261,399 A | | 11/1993 | Klatz et al. | 607/104 |
| 5,262,451 A | | 11/1993 | Winters et al. | 523/112 |
| 5,269,758 A | | 12/1993 | Taheri | 604/96 |
| 5,275,595 A | | 1/1994 | Dobak, III | 606/23 |
| 5,279,598 A | | 1/1994 | Sheaff | 604/290 |
| 5,281,213 A | | 1/1994 | Milder et al. | 606/15 |
| 5,281,215 A | | 1/1994 | Milder | 606/20 |
| 5,324,286 A | | 6/1994 | Fowle | 606/23 |
| 5,338,770 A | | 8/1994 | Winters et al. | 523/112 |
| 5,342,301 A | | 8/1994 | Saab | 604/96 |
| 5,342,693 A | | 8/1994 | Winters et al. | 428/447 |
| 5,354,277 A | | 10/1994 | Guzman et al. | 604/113 |
| 5,411,477 A | | 5/1995 | Saab | 604/96 |
| 5,423,807 A | | 6/1995 | Milder | 606/20 |
| 5,437,673 A | | 8/1995 | Baust et al. | 606/23 |
| 5,452,582 A | | 9/1995 | Longsworth | 62/51.2 |
| 5,478,309 A | | 12/1995 | Sweezer et al. | 604/4 |
| 5,486,204 A | | 1/1996 | Clifton | 607/96 |
| 5,486,208 A | | 1/1996 | Ginsberg | 607/106 |
| 5,531,776 A | | 7/1996 | Ward et al. | 607/105 |
| 5,545,161 A | | 8/1996 | Imran | 606/41 |
| 5,562,606 A | | 10/1996 | Huybregts | 604/8 |
| 5,609,620 A | | 3/1997 | Daily | 607/105 |
| 5,624,392 A | | 4/1997 | Saab | 604/43 |
| 5,655,548 A | | 8/1997 | Nelson et al. | 128/898 |
| 5,656,420 A | | 8/1997 | Chien | 435/1.2 |
| 5,693,080 A | | 12/1997 | Wallstén et al. | 607/105 |
| 5,702,435 A | | 12/1997 | Maytal | 607/104 |
| 5,716,386 A | | 2/1998 | Ward et al. | 607/106 |
| 5,730,720 A | * | 3/1998 | Sites et al. | 604/27 |
| 5,733,319 A | | 3/1998 | Neilson et al. | 607/105 |
| 5,735,809 A | | 4/1998 | Gorsuch | 604/4 |
| 5,758,505 A | | 6/1998 | Dobak, III et al. | 62/6 |
| 5,759,182 A | | 6/1998 | Varney et al. | 606/21 |
| 5,787,715 A | | 8/1998 | Dobak, III et al. | 62/51.2 |
| 5,837,003 A | | 11/1998 | Ginsberg | 607/106 |
| 5,848,991 A | | 12/1998 | Gross et al. | 604/140 |
| 5,916,242 A | * | 6/1999 | Schwartz | 607/113 |
| 5,997,501 A | * | 12/1999 | Gross et al. | 604/65 |
| 6,095,992 A | * | 8/2000 | Augustine | 602/2 |

* cited by examiner

AUTOMATIC FEVER ABATEMENT SYSTEM

BACKGROUND OF THE INVENTION

1. Field of the Invention

The present invention relates to a system that abates fever in hospital patients by administering medication, coolant, or other treatment substance.

2. Description of the Related Art

In warm blooded creatures, temperature regulation is one of the most important functions of the body. The human body seeks to maintain a core temperature of 37 degrees Celsius, and functions optimally when this temperature is achieved. Excessive temperatures cause various health problems, one of the most serious being brain damage. For patients with brain injury, fever can exacerbate neuronal outcomes.

To treat fever, a number of different techniques are known. For example, patients often receive medication such as acetaminophen (Tylenol) or acetylsalicylic acid (aspirin). In one extreme technique, physicians cool the patient's entire body by packing it in ice. In another technique, the patient is covered with a cooling blanket, such as an inflatable cushion that is filled with a coolant such as air or water. There are also other traditional approaches such a gastric lavage with ice water, infusing cold solution, etc.

One newly developed approach treats fever by circulating a coolant through a catheter placed inside a patient's body. The catheter may be inserted into veins, arteries, cavities, or other internal regions of the body. The present assignee has pioneered a number of different cooling catheters and techniques in this area. Several different examples are shown in U.S. application Ser. No. 09/133,813, which was filed on Aug. 13, 1998, U.S. Pat. No. 6,338,727 and is hereby incorporated into the present application by reference.

Regardless of which technique is ultimately used to treat a patient's fever, each of these techniques is manually activated by medical staff when they initially detect fever. Accordingly, some attention is required of medical staff in order to initially detect the onset of fever. This approach is therefore subject to some delay from the time medical staff recognize the start of fever until treatment is initiated. Importantly, the delay in applying treatment is a missed opportunity to prevent the fever in the first place. Moreover, during this delay, the fever may proceed into more serious stages. Thus, this delay can represent some health risk to the patient. As the science of medicine is interested in minimizing or reducing health risks wherever possible, the present Assignee realizes that known fever abatement approaches may not be completely satisfactory.

SUMMARY OF THE INVENTION

Broadly, the present invention concerns a machine-driven system to treat or even prevent fever in hospital patients by administering medication, coolant, or other treatment substance. One exemplary system includes a treatment substance administration path ("path"), a flow device, a source, one or more fever characteristic sensors, and a controller. The path may be an open-ended structure, such as a tube, or a closed-ended structure such as a catheter with a sealed, internal conduit. The treatment substance administration path is coupled to regions of the patient's body that will contain or absorb the treatment substance, as appropriate to the particular substance being used. The path is coupled to the flow device, which is itself attached to the source. The flow device comprises a pump, valve, or other suitable mechanism to regulate flow of the treatment substance from the source through the path. The source contains a treatment substance such as medication (in the case of an open-ended path) or a coolant (in the case of a closed-ended path). One or more fever characteristic sensors are attached to various sites on the patient. In the case of a closed-ended path, the system may also include a return vessel to receive treatment substance returning from the patient's body.

The fever characteristic sensors repeatedly measure temperature, metabolic rate, and/or other bodily properties that are affected by fever, and provide representative machine-readable outputs. Concurrently, the controller repeatedly computes a supply strategy to regulate the patient's temperature according to pre-programmed specifications. Then, according to the computed strategy, the controller directs the flow device to deliver treatment substance to the path, and ultimately to the patient's body. In addition to administering coolant, medication, or other treatment substance to treat fever, the controller may activate other antipyretic means by (1) starting, adjusting, or redirecting a fan, (2) adjusting an air conditioning thermostat, (3) issuing visual or audible warning signals to hospital staff, etc.

In one embodiment, the invention may be implemented to provide a method to automatically treat or prevent fever in hospital patients by administering medication, coolant, or other antipyretic treatment substance. In another embodiment, the invention may be implemented to provide an apparatus, such as fever abatement system, for automatically treating or preventing fever in hospital patients. In still another embodiment, the invention may be implemented to provide a signal-bearing medium tangibly embodying a program of machine-readable instructions executable by a digital data processing apparatus to perform operations to manage components of an automatic fever abatement system. Another embodiment concerns logic circuitry having multiple interconnected electrically conductive elements configured to perform operations to manage components of an automatic fever abatement system.

The invention affords its users with a number of distinct advantages. In addition to quickly recognizing the presence or future onset of fever, the invention automatically initiates a procedure to cool the patient. Unlike the prior art, there is no delay before medical staff recognize the start of fever. In fact, actions may be taken before the body even exhibits any temperature rise. With the invention, rapid delivery of a therapeutic drug can begin within minutes from fever recognition. As another benefit, the invention utilizes machine control to minimize operator supervision, and thereby reduces operating costs and frees medical staff for other duties. Accordingly, the prompt recognition and treatment of fever no longer requires twenty-four hour, minute-by-minute attention from hospital staff and doctors. As still another advantage, fever detection characteristics may be customized for each patient to ensure early and accurate fever detection. The invention also provides a number of other advantages and benefits, which should be apparent from the following description of the invention.

DETAILED DESCRIPTION

Figure 1A:
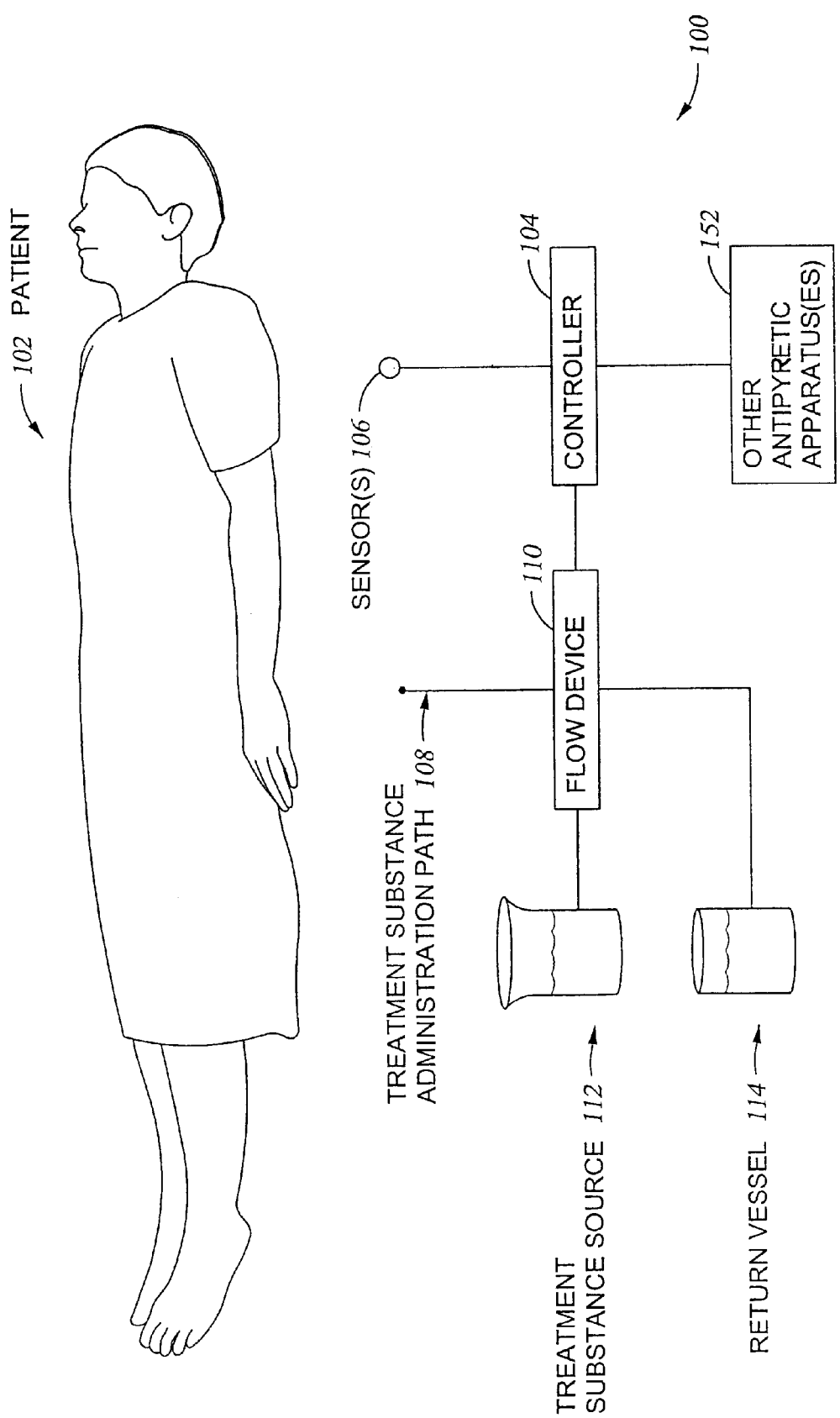
FIG. 1A is a schematic diagram of a fever abatement system according to the invention.

The nature, objectives, and advantages of the invention will become more apparent to those skilled in the art after considering the following detailed description in connection with the accompanying drawings.

Hardware Components & Interconnections
Automated Fever Abatement System
Introduction One aspect of the invention concerns a machine-driven system to treat or prevent fever in hospital patients by administering medication, coolant, or other antipyretic means. This system may be implemented in various ways, one example being shown by the hardware components and interconnections shown by the system 100 of FIG. 1. The system 100 includes a controller 104, one or more fever characteristic sensors 106, a flow device 110, a treatment substance administration path 108, and a source 112. The system 100 is utilized to automatically treat or even prevent fever in the patient 102.

Fever Characteristic Sensor(s)

As mentioned above, the system 100 includes one or more fever characteristic sensor(s) 106. As used herein, "fever" is defined as bodily temperature that is above normal due to pathogens or other stimuli. The system of this invention may be configured to detect fever; more advantageously from the standpoint of preventing fever, the invention may be configured to predictively detect the future onset of fever. Utilizing the foregoing definition of fever, the presence of fever is easily determined by detecting an elevated body temperature. In this respect, the fever characteristic sensors 106 may include one or more temperature sensors, deployed in various regions of the body that accurately represent the temperature of the entire body, the body core, or a particular region. As an example, a single temperature sensor may be deployed at the esophagus, bladder, tympanic membrane, rectum, or another local site that is representative of the body's core temperature. With multiple temperature sensors, the sensors may be distributed at various sites, and the resulting measurements averaged to provide a more accurate representation of the patient's temperature.

Advantageously, the fever characteristic sensors 106 may also include other sensors to detect the onset of fever. Since fever is preceded by increased metabolic rate, the sensors 106 may also include devices to detect increased oxygen consumption, increased carbon dioxide in exhaled air, decreased venous hemoglobin oxygen saturation, and the like. In the case of oxygen consumption or carbon dioxide measurement, the sensors 106 may comprise a gas analyzer coupled to automatic ventilation equipment or an open mask apparatus. In the case of venous hemoglobin oxygen measurement, relevant sensors 106 may comprise optical light reflectance and/or transmission devices, such as commercially available devices for detecting blood saturation.

Treatment Substance Administration Path

The treatment substance administration path 108 ("path") provides a means to administer a treatment substance to the patient. The path 108 may be open-end or closed-end. With an open-end path, the treatment substance takes a one-way trip into a region of the patient's body that is likely to absorb, distribute, or effectively process the treatment substance. The open-end treatment substance administration path, for example, may be routed to the patient's stomach, veins, arteries, esophagus, or rectum. The open-end path is advantageous for treatment substances that comprise medication, such as acetaminophen, in which case an exemplary treatment substance administration path may comprise a device such as nasogastric tube. FIG. 1C shows an exemplary open-end path 140. The path 140 comprises a conduit having a body 146 with an inlet 142 and an outlet 144. The open-end treatment substance administration path 140 is deployed by inserting the outlet 144 into an artery, vein, stomach, rectum, skin, lungs or other suitable body access point. Other examples of open-end path include a nasogastric tube, open-end catheter, intravenous needle, syringe, suppository, perforated tube for "drip" irrigation, transdermal patch, aerosol or other inhalant, etc.

In contrast to the open-end path, treatment substance circulates within the closed-end path without actually contacting the patient's body. This is beneficial if the treatment substance comprises a coolant such as saline. FIG. 1B shows an exemplary closed-end path 120, which is embodied by a cooling catheter. The catheter 120 includes a housing 122 having distal 128 and proximal 130 ends. The housing 122 contains a conduit 123 that runs from the catheter's proximal end 130 to the distal end 128 and back again. The conduit 123 has a supply opening 126 and a return opening 124. The conduit 123 therefore provides a round-trip path internal to the catheter 120, where this path is sealed from any contact with the patient's body. The closed-end path 120 is deployed by inserting the distal end 128 into a suitable blood vessel such as the inferior vena cava. A number of exemplary catheters and their use are described in U.S. application Ser. No. 09/321,515, which was filed on May 27, 1999 U.S. Pat. No. 6,165,201 and is hereby incorporated by reference into the present application.

Flow Device, Source, Return Vessel

The flow device 110 controls flow of the treatment substance from a source 112 to the patient to help prevent or abate the patient's fever. In one embodiment, the flow device 110 may comprise a pump or other structure that actively causes the treatment substance to flow through the path from the source 112, where the source comprises an intravenous bag, vial, jar, carton, box, or other storage facility. In another embodiment, the treatment substance flows by gravity and the flow device 110 comprises a valve, on-off switch, or other mechanism to regulate treatment substance flowing from the source 112. Here, the source 112 may comprise any intravenous bag, vial, jar, carton, box, or other storage facility, whether compressible or not. In still another embodiment, the source 112 has a dynamic volume and the treatment substance flows by reduction of the source's volume. Namely, the source 112 may be a self-compressed vessel (e.g., distended elastic container), or a compressible vessel whose volume decreases under external force (e.g., syringe, hydraulic vessel, compressible intravenous bag, chamber with piston-driven lid, etc.). In the case of a self-compressed source 112, the flow device 110 comprises a solenoid or other suitable device to regulate the amount of flow through the path; in the case of an externally compressed source 112, the flow device 110 comprises a compression mechanism such as a hydraulic pump, motor, piston, pinchers, screw-driven vise, etc. Ordinarily skilled artisans (having the benefit of this disclosure) will recognize a variety of other options to implement the flow device 110 and source 112.

In the case of an open-end path, the flow device 110 regulates flow of the treatment substance directly into the patient's body. In the case of a closed-end path, the flow device 110 regulates flow of the treatment substance into the supply opening (e.g., 126, FIG. 1B), and also collects spent treatment substance from the catheter's return opening (e.g., 124, FIG. 1B). The flow device 110 deposits returned treatment substance into the return vessel 114. The return vessel 114 may be omitted when an open-end path is used, or if the return vessel 114 leads to, or is combined with, the source 112. When a closed-end path is used, equipment for cooling the treatment substance may be implemented at the source 112, the flow device 110, return vessel 114, or other suitable location. If desired, the path 108 may be configured to incorporate one or more fever characteristic sensors 106. For instance, a rectal temperature probe may be combined with a path designed for exposure or insertion of an antipyretic drug or suppository.

Other Antipyretic Apparatus(es)

In addition to the foregoing components, the controller 104 may be coupled to one or more additional controller-activated antipyretic apparatuses, whether related to the administration of treatment substance or not. Some examples include inflatable cooling blankets, oscillating or fixed fans, air conditioning thermostats for room air or bath water, etc.

Controller—Generally

The controller 104 receives measurements from the sensor(s) 106, and serves to regulate operation of the flow device 110 according to predetermined specifications. To implement this automatic control feature, the controller 104 comprises an electronic module such as logic circuitry, discrete circuit elements, or a digital data processing apparatus (computer) that executes a program of machine-readable instructions.

When implemented in logic circuitry or a computer, the controller 104 analyzes the patient's temperature and/or other fever characteristic signals utilizing the controller's own programming, and provides the resultant output signal to regulate the flow device 110. When implemented in discrete circuitry, the circuitry or the controller 104 processes the patient's fever characteristics with circuitry to provide a resultant output signal that regulates the flow device 110.

Controller—Digital Data Processing Apparatus

As mentioned above, one embodiment of the controller 104 is a digital data processing apparatus. This apparatus may be embodied by various hardware components and interconnections, one example appearing in FIG. 2. The apparatus 200 includes a processor 202, such as a microprocessor or other processing machine, coupled to a storage 204. In the present example, the storage 204 includes a fast-access storage 206, as well as nonvolatile storage 208. The fast-access storage 206 may comprise random access memory (RAM), and may be used to store the programming instructions executed by the processor 202. The nonvolatile storage 208 may comprise, for example, one or more magnetic data storage disks such as a "hard drive", a tape drive, or any other suitable storage device. The apparatus 200 also includes an input/output 210, such as a line, bus, cable, electromagnetic link, or other means for the processor 202 to exchange data with other hardware external to the apparatus 200.

Despite the specific foregoing description, ordinarily skilled artisans (having the benefit of this disclosure) will recognize that the apparatus discussed above may be implemented in a machine of different construction, without departing from the scope of the invention. As a specific example, one of the components 206, 208 may be eliminated; furthermore, the storage 204 may be provided on-board the processor 202, or even provided externally to the apparatus 200.

Controller—Logic Circuitry

In contrast to the digital data storage apparatus discussed previously, a different embodiment of the invention implements the controller 104 with logic circuitry instead of computer-executed instructions. Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented using CMOS, TTL, VLSI, or another suitable construction. Other alternatives include a digital signal processing chip (DSP), discrete circuitry (such as resistors, capacitors, diodes, inductors, and transistors), field programmable gate array (FPGA), programmable logic array (PLA), and the like.

Operation

In addition to the structure described above, a different aspect of the invention concerns a process for automated fever abatement. As illustrated below, this process includes steps that are manually performed, such as preparing the patient for treatment. The process also includes automatic, machine-activated steps that treat or even prevent the patient's fever.

Signal-Bearing Medium

Figure 1B:
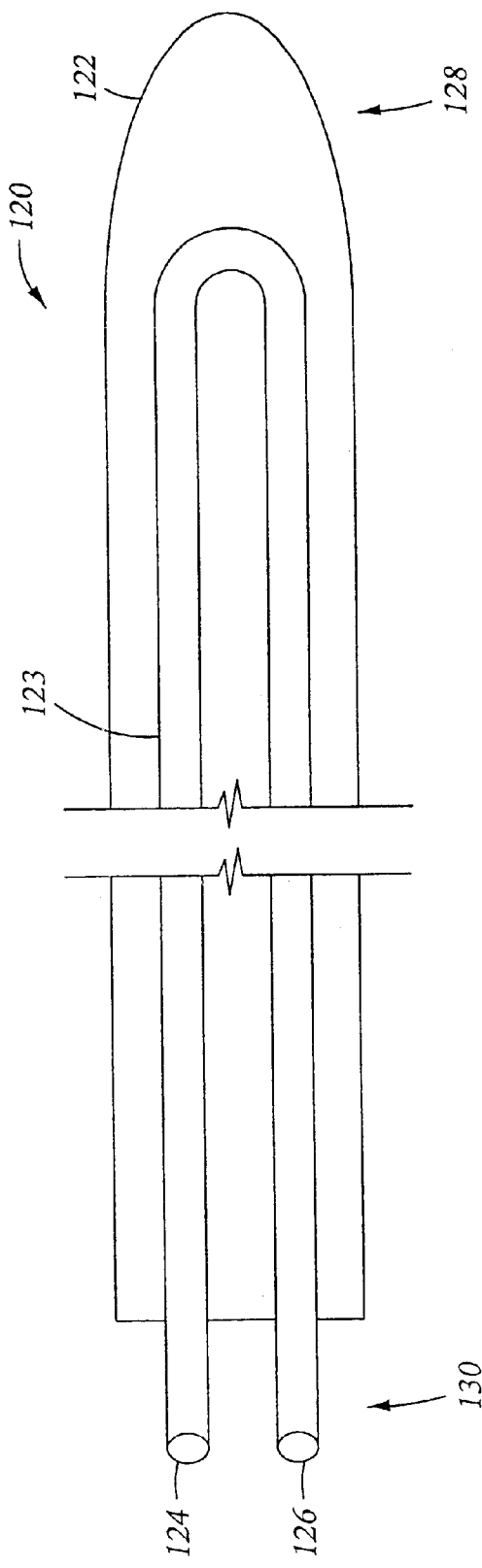
FIG. 1B is a diagram of a closed-end treatment substance administration path according to the invention.
Figure 1C:
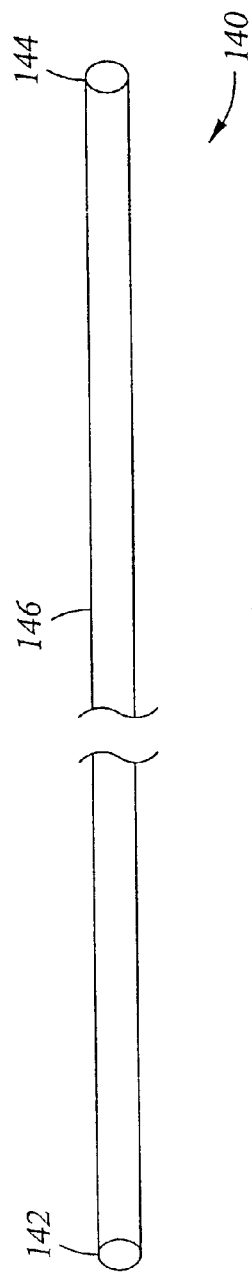
FIG. 1C is a diagram of an open-end treatment substance administration path according to the invention.
Figure 2:
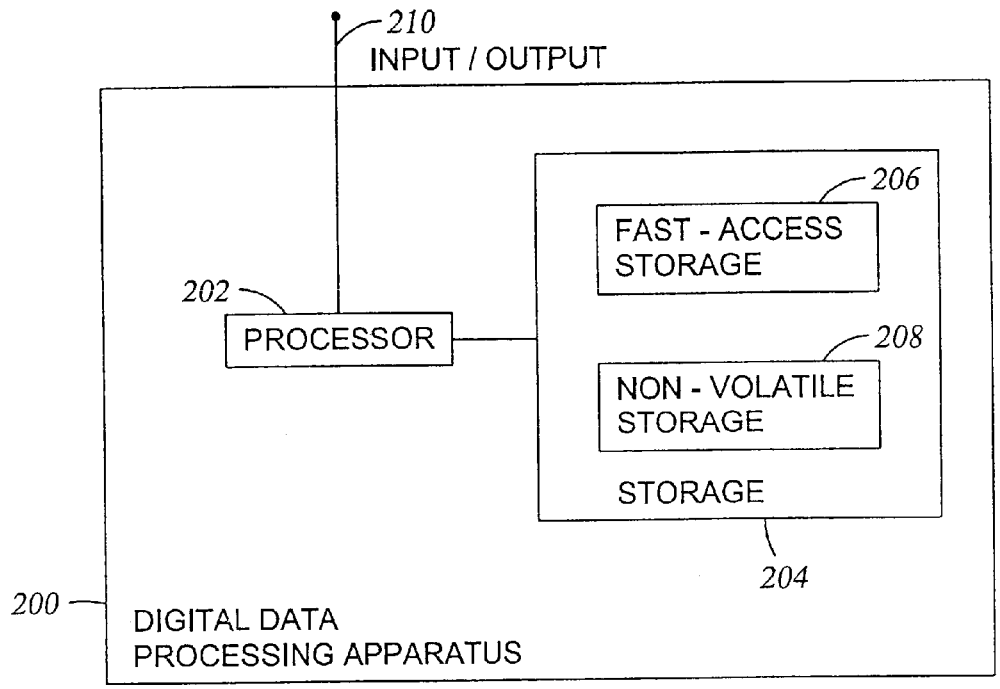
FIG. 2 is a diagram of a digital data processing apparatus according to the invention.

In the context of FIGS. 1–2, the automated fever abatement process may be implemented, for example, by operating the controller 104, as embodied by a digital data processing apparatus 200, to execute a sequence of machine-readable instructions. These instructions may reside in various types of signal-bearing media. In this respect, one aspect of the present invention concerns a programmed product, comprising signal-bearing media tangibly embodying a program of machine-readable instructions executable by a digital data processor to operate the system 100 to perform automated fever abatement.

Figure 3:
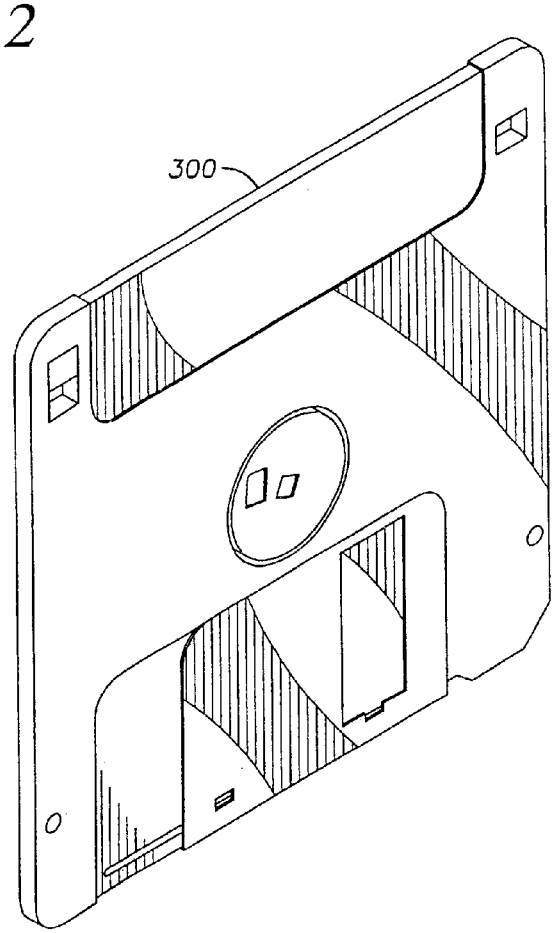
FIG. 3 shows an exemplary signal-bearing medium according to the invention.

This signal-bearing media may comprise, for example, RAM (not shown) contained within the controller 104, as represented by the fast-access storage 206, for example. Alternatively, the instructions may be contained in another signal-bearing media, such as a magnetic data storage diskette 300 (FIG. 3), directly or indirectly accessible by the processor 202. Whether contained in the diskette 300, storage 204, or elsewhere, the instructions may be stored on a variety of machine-readable data storage media, such as direct access storage (e.g., a conventional "hard drive," redundant array of inexpensive disks (RAID), or another direct access storage device (DASD)), magnetic tape, electronic read-only memory (e.g., ROM, EPROM, or EEPROM), optical storage (e.g., CD-ROM, WORM, DVD, digital optical tape), paper "punch" cards, or other suitable signal-bearing media including transmission media such as digital and analog and communication links and wireless. In an illustrative embodiment of the invention, the machine-readable instructions may comprise software object code, compiled from a language such as "C," etc.

Logic Circuitry

In contrast to the signal-bearing medium discussed above, the method of automated fever abatement may be implemented using logic circuitry, without using a processor to execute instructions. In this embodiment, the logic circuitry is implemented in the controller 104, and serves to perform an operational sequence according to this invention as described below. The logic circuitry may be implemented using many different types of circuitry, as discussed above.

Overall Sequence of Operation

Figure 4:
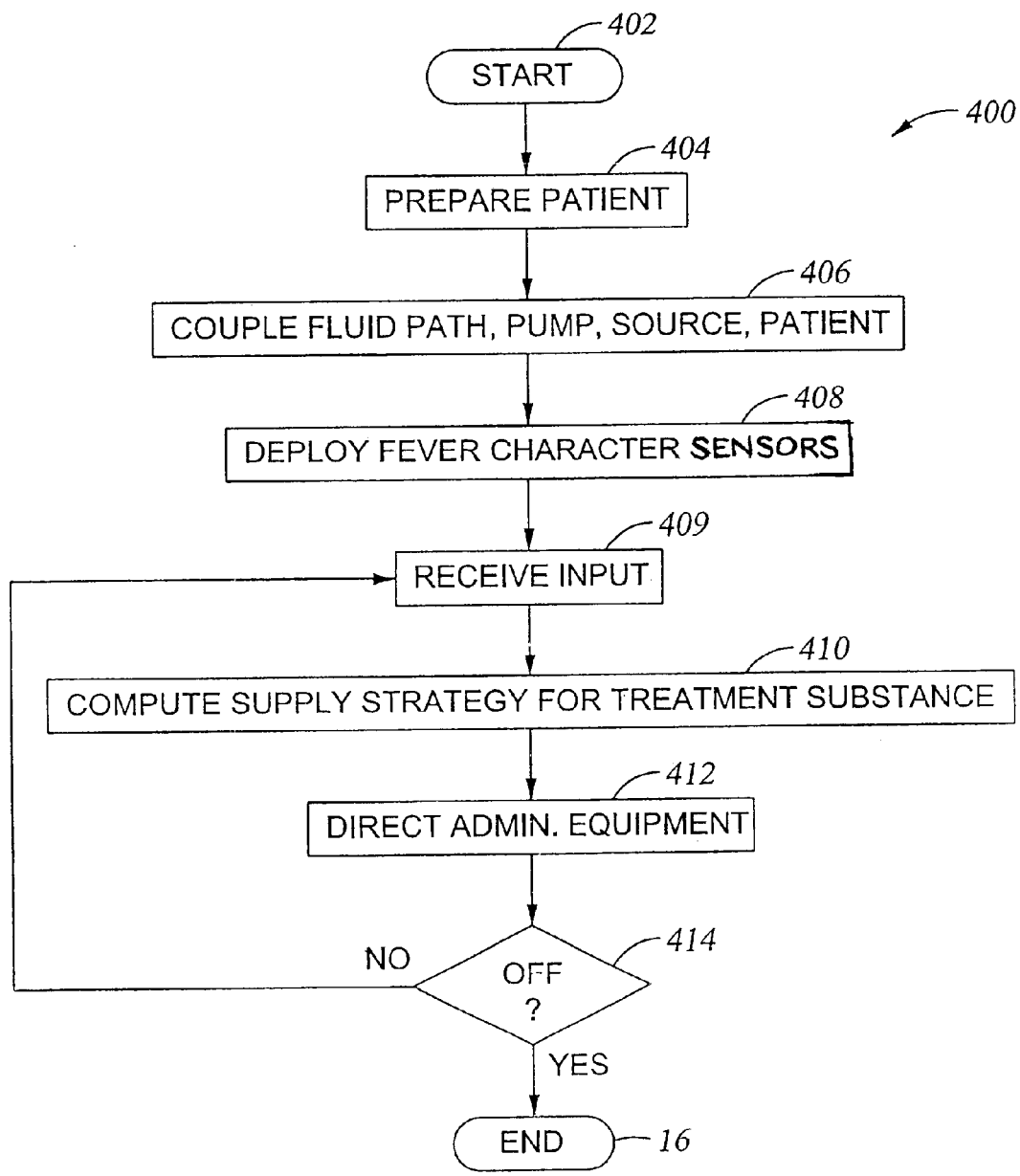
FIG. 4 is a flowchart of an operating sequence for automated fever abatement according to the invention.

FIG. 4 shows a sequence 400 that illustrates one example of the method aspect of the present invention. For ease of explanation, but without any intended limitation, the example of FIG. 4 is described in the context of FIGS. 1–2, as described above. After the sequence 400 is initiated in step 402, medical staff prepare the patient for treatment (step 404). As an example, such preparation may involve bathing, shaving, dressing, and other activities. Next, medical staff interconnect the components of the system 100 and deploy the path 108 to the appropriate bodily site(s) (step 406). Alternatively, if the system 100 components are pre-assembled, the assembly steps are omitted. After step 406, medical staff deploy the fever characteristic sensor(s) 106 at target regions of the patient's body. Upon completion of step 406, the sensors begin to measure the relevant physiological characteristics and provide representative machine-readable outputs.

As illustrated, steps 404, 406, and 408 are performed manually. As described below, however, steps 409, 410, 412, and 414 are performed by the controller 104 and serve to implement an automated method of fever abatement. In step 409, the controller 104 collects input for use in deciding how to operate the flow device 110 and thereby regulate the patient's temperature. Among other possible input, the input of step 409 includes input from the sensor(s) 106, such as body temperature, metabolic rate, and other bodily characteristics affected by fever. The input may also include other information such as (1) whether the path 108 is closed-end or open-end, (2) if the path 108 is open-end, the strength of the medication that constitutes the treatment substance, (3) the volume output of the flow device 110, (4) the patient's temperature history, (5) the history of treatment substance application with the current patient, (6) any post-delivery time delay required for treatment substance to take effect, and (7) other such factors.

After step 409, the controller computes a supply strategy in step 410. The supply strategy specifies a volume, timing, and rate of treatment substance supply that is calculated to regulate the patient's temperature according to predetermined specifications. These predetermined specifications are pre-programmed into the controller 104. As an example, the predetermined specifications may dictate keeping the patient's core temperature at or below 37.5 degrees Celsius, limiting any temperature excursions to a maximum time or temperature, etc.

Thus, the supply strategy constitutes the manner of treatment substance delivery that will achieve the predetermined specifications. To compute the supply strategy, the controller 104 considers the input from step 409 and applies a predetermined analysis to this data. The predetermined analysis may be specified by one or more equations, lookup tables, or other machine-readable information available to the controller 104 by software programming, hardware configuration, etc.

To illustrate step 410 in greater detail some examples are provided. In a first example, the path 108 is closed-end and the treatment substance comprise room temperature or cooled saline, and the predetermined specifications require keeping the patient's core temperature below 37.5 degrees Celsius. Here, one example of the controller's strategy is (1) operating the flow device 110 to circulate coolant if the patient's temperature reaches 37.5 degrees Celsius, and (2) ceasing operation of the flow device 110 whenever the patient's temperature is below 37.5 degrees Celsius.

In a second example, the path 108 is open-end and the treatment substance comprises one or more antipyretic drugs such as acetaminophen, aspirin, naproxen, ibuprofen, etc. In this example, the controller 104 may compute a strategy that activates the flow device 110 to administer a bolus of the treatment substance upon detecting fever or febral onset. Bolus may be especially desirable because fever tends to occur in spikes with rapid onset, and rapid initial delivery in a bolus may rapidly establish a meaningful blood concentration of the antipyretic treatment substance.

As an alternative strategy, an initial bolus of one drug may be administered, and if fever persists, a second larger bolus of the same drug or a bolus of a second antipyretic drug is administered. Furthermore, once fever is detected (or febral inset predicted), the treatment substance may be administered with an increasing rate if a preset body temperature is reached or if a predetermined rate of temperature increase is detected.

After the supply strategy is computed in step 410, the controller 104 directs the administration equipment 100 to implement this strategy in step 412. Namely, the controller 104 directs the flow device 110 to begin delivering the treatment substance to the path 108 according to the computed supply strategy. Where the flow device 110 comprises a valve, step 412 involves opening, closing, or adjusting constriction of the valve. Where the flow device 110 is a pump, the flow rate may be controlled by varying pump speed or repeatedly turning a constant-speed pump on and off. Also in step 412, the controller 104 may record the time that treatment began for subsequent documentation by nurses, etc.

In step 414, the controller 104 determines whether it has received an "off" command. The "off" command may be received by keyboard entry, manual activation of a switch (not shown) coupled to the controller 104, expiration of a pre-programmed treatment period, etc. If the "off" command has not been received, the sequence 400 returns to step 409, whereupon the controller 104 receives further input from the sensors 106, adjusts the supply strategy if necessary (step 410), and directs the components of the system 100 accordingly (step 412). When step 414 receives the "off" command, the routine 400 ends in step 416.

Other Embodiments

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated.

What is claimed is:

1. A method for treating fever in a warm blooded patient, the method comprising operations of:
    deploying a treatment substance administration path at one or more bodily sites of the patient;
    coupling the path to a flow device configured to selectively deliver a treatment substance;
    deploying one or more fever characteristic sensors at one or more bodily sites of the patient;
    operating the sensors to repeatedly measure fever-affected physiological characteristics of the patient and provide representative machine-readable outputs;
    a controller receiving the outputs;
    in response to prescribed input including predetermined values of the outputs, the controller computing a supply strategy to regulate the patient's temperature according to predetermined specifications, where the predetermined values of the outputs indicate future onset of fever; and the controller directing the flow device to deliver the treatment substance to the patient via the path according to the computed supply strategy.

2. A signal-bearing medium tangibly embodying a program of machine-readable instructions executable by a digital processing apparatus to perform operations for treating fever in a warm-blooded patient, the operations comprising:

repeatedly receiving machine-readable outputs from one or more fever characteristic sensors deployed at one or more bodily sites of the patient, the outputs representing physiological fever-affected characteristics of the patient;

in response to prescribed input including predetermined values of the outputs, where the predetermined values of the outputs indicate future onset of fever, computing a supply strategy to regulate the patient's temperature according to predetermined specifications; and according to the computed supply strategy, directing a machine-activated flow device to deliver a treatment substance to the patient via a treatment substance administration path deployed at one or more bodily sites of the patient.

3. A logic circuit of multiple interconnected electrically conductive elements configured to perform operations for treating fever in a warm blooded patient, the operations comprising:

repeatedly receiving machine-readable outputs from one or more fever characteristic sensors deployed at one or more bodily sites of the patient, the outputs representing physiological fever-affected characteristics of the patient;

in response to prescribed input including predetermined values of the outputs, where the predetermined values of the outputs indicate future onset of fever, computing a supply strategy to regulate the patient's temperature according to predetermined specifications; and according to the computed supply strategy, directing a machine-activated flow device to deliver a treatment substance to the patient via a treatment substance administration path deployed at one or more bodily sites of the patient.

4. An apparatus to treat fever in a warm blooded patient, the apparatus comprising:

a treatment substance administration path to direct a treatment substance to one or more bodily sites of the patient;

a flow device configured to selectively deliver the treatment substance from a source to the path;

one or more fever characteristic sensors repeatedly measuring fever-affected physiological characteristics of the patient and providing representative machine-readable outputs; and a controller coupled to the flow device and the sensors, the controller being configured to regulate body temperature of the patient by performing operations including: receiving the machine-readable outputs; responsive to prescribed input including predetermined values of the outputs, the controller being configured such that the predetermined values of the outputs indicate future onset of fever, computing a supply strategy to regulate the patient's temperature according to predetermined specifications; and directing the flow device to deliver the treatment substance to the patient via the path according to the computed supply strategy.

5. A method for treating fever in a warm blooded patient the method comprising the steps of:

providing a treatment substance administration path including one of a catheter and tube;

providing a flow device configured to selectively deliver a treatment substance to the path;

deploying the treatment substance administration path to at least one bodily site of the patient, each of the at least one bodily site being disposed either hypodermically beneath the patient's dermis or being accessible through a naturally occurring orifice of the patient;

deploying at least one fever-characteristic sensor to at least one bodily sensor site of the patient;

operating the at least one sensor to repeatedly measure at least one fever-affected physiological characteristic of the patient and provide at least one machine-readable sensor output indicative of the at least one fever-affected physiological characteristic; and operating a controller to receive the at least one sensor output as controller input, to compute a supply strategy to regulate the patient's temperature according to predetermined specifications and in response to prescribed controller input including predetermined values of at least one of the at least one sensor output, and to direct the flow device to deliver the treatment substance to the patient via the path according to the computed supply strategy and wherein the predetermined values of the at least one of the at least one sensor output Indicating future onset of fever.

6. A logic circuit of multiple interconnected electrically conductive elements configured to perform operations for treating fever in a warm-blooded patient, the operations comprising:

repeatedly receiving as input at least one machine-readable sensor output from at least one fever-characteristic sensor deployed to at least one bodily sensor site of the patient, at least one of the at least one sensor output being indicative of at least one physiological fever-affected characteristic of the patient;

in response to prescribed input including predetermined values of at least one sensor output, computing a supply strategy to regulate the patient's temperature according to predetermined specifications; and according to the computed supply strategy, directing a machine-activated flow device to deliver a treatment substance to the patient via a treatment substance administration path deployed to at least one bodily site of the patient, the treatment substance administration path including one of a catheter and tube, each of the at least one bodily site being disposed either hypodermically beneath the patient's dermis or being accessible through a naturally occurring orifice of the patient and wherein the predetermined values of at least one of the at least one sensor output indicating future onset of fever.

7. An apparatus for treating fever in a warm-blooded patient, the apparatus comprising:

a treatment substance administration path including one of a catheter and tube, the treatment substance administration path for directing a treatment substance to at least one bodily site of the patient, each of the at least one bodily site being disposed either hypodermically beneath the patient's dermis or being accessible through a naturally occurring orifice of the patient;

a flow device configured to selectively deliver the treatment substance from a treatment substance source to the path;

at least one fever-characteristic sensor, each of the at least one sensor repeatedly sensing at least one fever-affected physiological characteristic of the patient and providing at least one machine-readable sensor output indicative of the at least one fever-affected physiological characteristic;

a controller configured to regulate the patient's temperature, the controller being coupled with the flow device and with at least one of the at least one sensor, the controller a) receiving as controller input at least one of the at least one machine-readable sensor output, b) responsive to prescribed controller input including at least one predetermined value of at least one sensor output, computing a supply strategy to regulate the patient's temperature according to at least one predetermined specification, and c) directing the flow device to deliver the treatment substance to the patient via the path according to the computed supply strategy and wherein at least one predetermined value of at least one of the at least one sensor output indicating future onset of fever.

* * * * *